United States Patent
Steingart et al.

(10) Patent No.: US 8,509,933 B2
(45) Date of Patent: *Aug. 13, 2013

(54) FABRICATION OF NON-HOMOGENEOUS ARTICLES VIA ADDITIVE MANUFACTURING USING THREE-DIMENSIONAL VOXEL-BASED MODELS

(75) Inventors: Robert Steingart, Wellesley, MA (US); David Tzu-Wei Chen, Wrentham, MA (US)

(73) Assignee: 3D Systems, Inc., Rock Hill, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/462,503

(22) Filed: May 2, 2012

(65) Prior Publication Data

US 2012/0219698 A1 Aug. 30, 2012

Related U.S. Application Data

(63) Continuation of application No. 13/208,992, filed on Aug. 12, 2011.

(60) Provisional application No. 61/373,785, filed on Aug. 13, 2010, provisional application No. 61/373,780, filed on Aug. 13, 2010, provisional application No. 61/426,839, filed on Dec. 23, 2010, provisional application No. 61/445,960, filed on Feb. 23, 2011.

(51) Int. Cl.
*G01M 1/38* (2006.01)

(52) U.S. Cl.
USPC ............................................. 700/98; 700/119

(58) Field of Classification Search
USPC .......................... 264/308; 700/118–120, 163
See application file for complete search history.

(56) References Cited

U.S. PATENT DOCUMENTS

| | | | |
|---|---|---|---|
| 6,111,577 A | 8/2000 | Zilles et al. | |
| 6,165,406 A * | 12/2000 | Jang et al. | 264/308 |
| 6,421,048 B1 | 7/2002 | Shih et al. | |
| 6,867,770 B2 | 3/2005 | Payne | |
| 6,958,752 B2 | 10/2005 | Jennings, Jr. et al. | |
| 7,149,596 B2 | 12/2006 | Berger et al. | |
| 2002/0167101 A1 * | 11/2002 | Tochimoto et al. | 264/40.1 |
| 2003/0175410 A1 * | 9/2003 | Campbell et al. | 427/2.24 |
| 2007/0150088 A1 * | 6/2007 | Silverbrook | 700/119 |
| 2008/0246761 A1 | 10/2008 | Faken et al. | |
| 2008/0261165 A1 | 10/2008 | Steingart et al. | |
| 2009/0248184 A1 | 10/2009 | Steingart et al. | |
| 2009/0287332 A1 * | 11/2009 | Adusumilli et al. | 700/98 |
| 2010/0291505 A1 | 11/2010 | Rawley et al. | |
| 2010/0323328 A1 * | 12/2010 | Brodkin et al. | 433/201.1 |

OTHER PUBLICATIONS

Michael Wang, Heterogeneous Object Slicing with Geometric Contour Constraint, 2009, p. 137-144.*
AMF Specification Draft v 0.45, published Jun. 23, 2010 at http://ccsi.mae.cornell.edu/sites/default/files/AMF_V0.45.pdf.

(Continued)

*Primary Examiner* — Mohammad Ali
*Assistant Examiner* — Nathan Laughlin

(57) ABSTRACT

The invention provides systems and methods for manufacture of a non-homogeneous article using a 3D voxel-based model of the article and a rapid prototyping device. Use of a voxel-based model provides processing advantages and offers improved realism of the manufactured object with regard to non-homogeneous (i) color, (ii) translucency, and/or (iii) hardness, for example.

16 Claims, 1 Drawing Sheet

(56) References Cited

OTHER PUBLICATIONS

Cornell Creative Machines Lab dated Feb. 21, 2013 at http://creativemachines.cornell.edu/amf.pdf.

Vijay Chandru et al., Voxel-Based Modeling for Layered Manufacturing, pp. 42-47, in IEEE Computer Graphics and Application, Nov. 1995, IEEE, Piscataway, NJ.

Miller et al., Development of anatomically Reallstic PET and PET/CT Phantoms with Rapid Protoyping Technology, pp. 4252-4257, IEEE Nuclear Science Symposium Conference Record, 2007, IEEE, Piscataway, NJ.

Third Party Preissuance Submission Descriptions of Relevance created by the Berkman Center for internet and Society of Harvard Law School for U.S. Appl. No. 13/462,503.

* cited by examiner

FABRICATION OF NON-HOMOGENEOUS ARTICLES VIA ADDITIVE MANUFACTURING USING THREE-DIMENSIONAL VOXEL-BASED MODELS

CROSS-REFERENCE TO RELATED APPLICATION

This application is a continuation of U.S. patent application Ser. No. 13/208,992, filed on Aug. 12, 2011, which claims priority to and the benefit of U.S. Provisional Patent Application No. 61/373,780, which was filed on Aug. 13, 2010, U.S. Provisional Patent Application No. 61/426,839, which was filed on Dec. 23, 2010, U.S. Provisional Patent Application No. 61/373,785, which was filed on Aug. 13, 2010, and U.S. Provisional Patent Application No. 61/445,960, which was filed on Feb. 23, 2011, the disclosures of which are hereby incorporated herein by reference in their entireties.

FIELD OF THE INVENTION

This invention relates generally to rapid prototyping (additive manufacturing) systems. More particularly, in certain embodiments, the invention relates to systems for manufacture of non-homogeneous articles using 3D voxel-based models and a rapid prototyping device.

BACKGROUND OF THE INVENTION

Rapid prototyping is used to construct physical objects, particularly prototype parts or small volume manufactured components. Rapid prototyping systems make use of additive manufacturing technology, wherein a machine uses digital data from a virtual model of the object and deposits successive layers or parcels of liquid, powder, or sheet material, corresponding to layers or parcels of the virtual model. The layers or parcels bind together (either upon contact or by application of heat and/or binding materials), and the part is thereby produced.

To date, there have been no commercial 3D printers capable of rapid manufacture of realistic-looking, aesthetic teeth, veneers, or other dental implants. This largely has to do with the variation in color, translucency, hardness, and other properties within a tooth, and the difficult of manufacturing a close replica of such a complex organic object.

The optical properties of a solid material are defined by the way in which light waves interact with it through absorption, scattering, reflection, transmittance and refraction. When white light is incident on a solid material, its color is defined by which frequencies are absorbed, and which are reflected back (or transmitted, in the case of glass) to an observer. The reflection can be either reflective, in which case the object will have a specular or glossy appearance, or diffusive, in which the object will appear to have a more matte finish.

Tooth enamel, dentin, cementum, and dental pulp are four major tissues which make up the tooth in vertebrates. Enamel is the hardest and most highly mineralized substance in the human body. Enamel is the visible dental tissue of a tooth because it covers the anatomical crown and is supported by the underlying dentin. Ninety-six percent of enamel is mineral, with water and organic material composing the rest. In humans, enamel varies in thickness over the surface of the tooth, often thickest at the cusp, up to 2.5 mm, and thinnest at its border with the cementum at the cementoenamel junction (CEJ). The normal color of enamel varies from light yellow to grayish white. At the edges of teeth where there is no dentin underlying the enamel, the color sometimes has a slightly blue tone. Since enamel is semi-translucent, the color of dentin and any material underneath the enamel strongly affects the appearance of a tooth.

Enamel's primary mineral is hydroxylapatite, which is a crystalline calcium phosphate. The large amount of minerals in enamel accounts not only for its strength but also for its brittleness. Tooth enamel ranks 5 on Mohs hardness scale and a Young's modulus of 83 GPa. Dentin, less mineralized and less brittle, 3-4 in hardness, compensates for enamel and is necessary as a support. On X-rays, the differences in the mineralization of different portions of the tooth and surrounding periodontium can be noted; enamel appears more radiopaque (or lighter) than either dentin or pulp since it is denser than both, both of which appear more radiolucent (or darker).

Enamel does not contain collagen, as found in other hard tissues such as dentin and bone, but it does contain two unique classes of proteins—amelogenins and enamelins. While the role of these proteins is not fully understood, it is believed that they aid in the development of enamel by serving as a framework for minerals to form on, among other functions. Once it is mature, enamel is almost totally absent of the softer organic matter. Enamel is avascular and has no nerve supply within it and is not renewed, however, it is not a static tissue as it can undergo mineralization changes.

Optical transparency in polycrystalline materials is limited by the amount of light which is scattered by their microstructural features. Light scattering depends on the wavelength of the light. Limits to spatial scales of visibility (using white light) therefore arise, depending on the frequency of the light wave and the physical dimension of the scattering center. For example, since visible light has a wavelength scale on the order of a micrometer, scattering centers will have dimensions on a similar spatial scale. Primary scattering centers in polycrystalline materials include microstructural defects such as pores and grain boundaries.

The hardness of a solid material is determined by its microstructure, or the structure and arrangement of the atoms at the atomic level. At the atomic level, the atoms may be arranged in an orderly three-dimensional array called a crystal lattice. However, a given specimen of a material likely never contains a consistent single crystal lattice. The material will likely contain many grains, with each grain having a fairly consistent array pattern. At a smaller scale, each grain contains irregularities. It is these irregularities at the grain level of the microstructure that are responsible for the hardness of the material.

When considering the rapid manufacture of non-homogeneous articles, such as teeth, material parameters need to be precisely controlled throughout the print volume in order to achieve an aesthetically acceptable result, since those parameters vary throughout the volume of the object. For example, color, translucency, hardness, elasticity, and the like, vary throughout the solid.

Current prototyping techniques employ Stereo Lithography File (STL) data structures (e.g., triangles or other polygons defining the surface of the object) that rapid prototyping machines use as input. Even in the simplest case where only a single parameter, such as color, varies throughout a solid, the required STL-based geometry is difficult to construct. For example, consider a red and white candy cane. Using STL geometry would first require defining the surface of the basic cane, then defining the complicated spiral shape of the red surface independently; and then performing a constructive-solid-geometry operation to define the white surface through a subtraction.

There is a need for improved methods for rapid prototyping of non-homogenous objects.

Volumetric representations readily maintain a watertight model without holes or self-intersections. Such representations naturally support Boolean operations based on a voxel-by-voxel compositing process. A voxel is a volume element. In order to perform the methods of the invention, an initial model is created. This model comes from various sources including scans of physical objects or prior interactive editing. The voxel model, or an alternative initial model, is represented by numerical values maintained in computer memory in an array.

SUMMARY OF THE INVENTION

Systems and methods are provided for the fabrication of non-homogeneous articles via additive manufacturing using three-dimensional voxel-based models. These systems and methods make it possible to rapidly build a prototype, or perform small volume manufacture, of an article that has varying colors, shades, textures, and/or other properties throughout the article.

For example, a tooth has a variety of portions having different properties, e.g., the enamel, dentin, pulp, cementum, and root of a tooth have different color, translucency, hardness, etc. A property that varies throughout the article (e.g., color) can be represented by assigning each voxel in a virtual model of the article a value corresponding to that property. The rapid prototyping machine then deposits material on a voxel-by-voxel basis (or parcel-by-parcel basis, if more than one voxel is grouped at a time), such that the deposited material in each voxel has the property value (e.g., color) assigned to that voxel.

An artificial tooth for use in a set of dentures is one example of a heterogeneous (i.e., non-homogeneous) article that can be quickly fabricated using the systems and methods described herein. Other examples include jewelry, footwear, industrial parts, automotive parts, medical devices, and prosthetics, to name a few.

In one aspect, the invention relates to a method for manufacturing an aesthetically-acceptable non-homogeneous object (e.g., one or more teeth). The method includes the steps of: (a) defining a 3D voxel representation for the non-homogeneous object to be manufactured, wherein each of a plurality of voxels is assigned one or more values representing one or more of the following prescribed physical properties M: color, translucency, and hardness; (b) using the 3D voxel representation to (i) define a set of 3D dots to produce a shape of each of a plurality of successive Z-layers of the object to be manufactured, and (ii) define the one or more prescribed physical properties at each dot making up each of the successive Z-layers of the object to be manufactured; (c) defining a transfer function T(M) that identifies a pigment, a resin, or both a pigment and a resin to produce a material having the one or more prescribed physical properties for each 3D dot to be printed; and (d) using a 3D printer (e.g., a rapid prototyping device) to deposit the pigment and/or the resin identified by the transfer function at each dot of each of the plurality of successive Z-layers of the object, thereby producing the non-homogeneous object.

In certain embodiments, step (b) includes using multivariate interpolation (e.g., trilinear interpolation) to define the one or more prescribed physical properties at each 3D dot. In one embodiment, the transfer function T(M) identifies multiple pigments and/or multiple resins. In another embodiment, a value of the one or more prescribed physical properties varies within the object and/or within each of the Z-layers of the object.

In certain embodiments, the one or more prescribed physical properties includes translucency, and step (d) includes depositing at least two different resins with embedded crystalline particles at a given dot, the combination of which resins produces the translucency prescribed for the given dot. The embedded crystalline particles may have a known size distribution. In one embodiment, one or more of the voxels has at least one associated real world dimension that is no greater than about 10 microns. In another embodiment, the 3D voxel representation defined in step (a) is partitioned into a hierarchy of blocks, wherein each block: (i) has one or more spatial properties in common; and/or (ii) has one or more of the prescribed physical properties in common.

In another aspect, the invention relates to a system for fabricating a non-homogeneous article. The system includes a user interface configured to receive input from a user; a design application in communication with the user interface, wherein the design application is configured to create a 3D voxel-based model of a non-homogeneous article, wherein each voxel is assigned one or more physical properties; and a rapid prototyping machine for fabrication of the non-homogeneous article, wherein said rapid prototyping machine is configured to fabricate the artificial tooth via additive manufacturing using the 3D voxel-based model, wherein properties of the voxels of the model correspond to properties of the voxels of the fabricated article.

In certain embodiments, the physical properties include at least one of color, translucency, hardness, modulus, and dynamic modulus. The system may be configured to perform additive manufacturing by providing successive layers or parcels of material.

BRIEF DESCRIPTION OF THE DRAWING

The objects and features of the invention can be better understood with reference to the drawing described below, and the claims.

While the invention is particularly shown and described herein with reference to specific examples and specific embodiments, it should be understood by those skilled in the art that various changes in form and detail may be made therein without departing from the spirit and scope of the invention.

DETAILED DESCRIPTION

Figure 1:
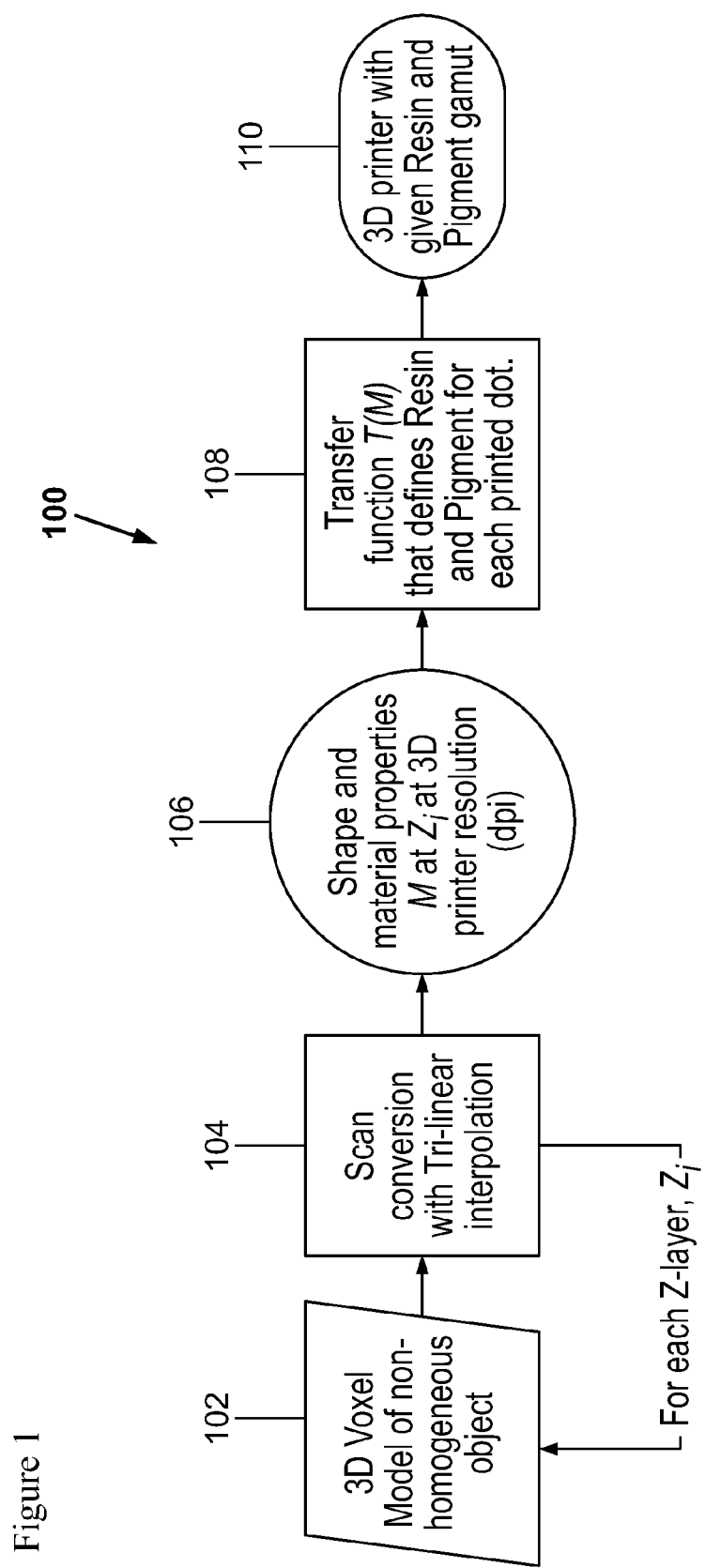
FIG. 1 is a flow chart for a method of manufacturing an aesthetically-acceptable non-homogeneous object, according to an illustrative embodiment of the invention.

It is contemplated that devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Previous prototyping techniques use STL-based geometry and therefore suffer significant limitations, even in producing simple, non-homogeneous objects, such as the candy cane example described above. However, a solution presented herein is to switch to a voxel-based modeling approach. By assigning one or more values to each voxel in the model that is reflective of physical properties that vary throughout the volume to be produced, it is much easier to produce high quality, aesthetically acceptable, non-homogenous objects. In the candy cane example discussed above, the cane shape may be first defined in voxels, then a 3D texture map applied to define the red portion of the candy cane by tagging the appropriate voxels, with the remaining untagged voxels defined as the white portion of the candy cane.

Further, a voxel representation lends itself to a more accurate, simpler, direct interface of model data with 3D printer output. Typically, for current STL-based output systems, the STL file is scan-converted to produce pixels at the printer's native resolution (dpi or dots per inch) one level at a time, thereby defining each successive Z-layer. However, voxels lend themselves to a more efficient, more direct interface with a 3D printer. For example, the shape and desired material properties of each successive Z-layer (depth layer) of the object to be manufactured can be defined by simple tagging of voxels. Values of one or more physical properties (e.g. color, translucency, hardness, elasticity, etc.) are then assigned for each voxel.

Also, voxel representations lend themselves to efficient processing, e.g., performance of multivariate (e.g., trilinear) interpolation to drive the printer output on demand and at the proper resolution. Moreover, in certain embodiments, a block coding scheme is utilized to represent spatial features of the 3D voxel models efficiently at a high resolution. For the case of production of aesthetic teeth, the resolution needed requires voxels no greater than about 10 microns in one, two, or three dimensions. Memory space need not be allocated for each voxel—such high resolution would require many megabytes of RAM. However, this obstacle is overcome in various embodiments, for example, by employing a block coding algorithm that partitions space into a hierarchy of blocks that share the same spatial value and/or material properties, In addition to the processing advantages, voxel representation offers improved realism of the produced object with regard to non-homogeneous (i) color, (ii) translucency, and/or (iii) hardness, for example.

Regarding color, pigments work by selectively absorbing certain wavelengths of light in the visible portion of the spectrum. The use of different pigments and/or different amounts of pigment among the various dots of each Z-layer of the object being 3D-printed allows representation of non-homogenous color. It is not necessary to design a rapid prototyping machine with every possible pigment necessary, but instead, primary colors can be combined to produce a full range of colors. For example, a combination of three pigments such as red, yellow, and blue, or a combination of primary ink colors such as cyan, magenta, yellow, and black (CMYK), or other combination of colors, may be prescribed for each 3D dot of each successive Z-layer laid down by the printer. A 3D dot can be any 3D structure that corresponds to one or more voxels.

The color mixing can happen in several ways. For example, in the Objet Geometries, Ltd., prototyping machine, the Connex500™, it is possible to jet and mix multiple resins simultaneously (Object Geometries, Let. Is headquartered in Rehovot, Israel, with U.S. office in Billerica, Mass.). In order to take advantage of the trichromatic effect, multiple resins are provided in the primary colors, and these are jetted and mixed in the proper proportion to produce a desired color for each 3D dot of each layer of the object. The Connex500™ uses a computer controlled print-head, similar to those used in standard, 2D, ink jet printers to create 3D objects one layer at a time.

In another embodiment, the structural component of each printed 3D dot is considered separately from its color. For example, a uniform resin "structural" material is mixed with the prescribed combination of primary pigment colors as each droplet is sprayed to produce a final colored three-dimensional shape.

Regarding translucency, in order to realistically replicate a translucent object, the volume fraction of microscopic pores in the manufactured object should be less than about 1% for high-quality optical transmission; that is, the material density should be at least about 99.99% of the theoretical crystalline density of the object (e.g., tooth, veneer, or dental implant) in order to provide a realistic, aesthetic manufactured object. Furthermore, most of the interfaces in a typical metal or ceramic object are in the form of grain boundaries which separate tiny regions of crystalline order. When the size of the scattering center (or grain boundary) is reduced below the size of the wavelength of the light being scattered, the scattering no longer occurs to any significant extent.

In the formation of polycrystalline materials (metals and ceramics) the size of the crystalline grains is determined largely by the size of the crystalline particles present in the raw material during formation (or pressing) of the object. Moreover, the size of the grain boundaries scales directly with particle size. Thus, a reduction of the original particle size well below the wavelength of visible light (about $\frac{1}{15}$ of the light wavelength or roughly 600/15=40 nm) eliminates much of light scattering, resulting in a translucent or even transparent material.

Thus, in order to simulate the semi-translucent scattering appearance of tooth enamel, the rapid manufacturing machine used should be able to control the size of the microstructural scattering centers. It is possible to embed crystalline particles in a photosensitive (UV) epoxy base resin for the purpose of stereolithography (SLA), for example, as has been done by DSM Somos of Elgin, Ill., for their NanoTool™ product.

A number of methods for controlling the scattering appearance of a non-homogenous article are presented herein. For example, an Objet Connex machine (e.g., Connex500™) features multiple resins that are mixed and jetted to produce a finished three-dimensional object. In certain embodiments of the present invention, two separate photosensitive resins can be provided with embedded crystalline particles of differing, but known sizes and/or size distributions. To produce a desired scattering effect would then involve mixing of these resins in the correct proportions.

Another approach for controlling the scattering appearance of a non-homogenous article uses stereolithography (SLA) in the rapid manufacturing/printing of the 3D object. For example, a single laser is used to trace and cure one layer of material at a time. This approach can be extended to include a vat with two or more different resins, with differing scattering center sizes, sensitive to different frequencies of light. Here, it is possible to control the scattering appearance of the non-homogeneous article by using multiple lasers of different wavelengths to selectively cure each of the resins individually. This particular method is also applicable to rapid manufacturing based on DLP (Digital Light Processor) projection by using multiple light sources with different wavelengths, such as employed by EnvisionTEC of Gladback, Germany, in its Perfactory® system.

Regarding hardness, as discussed previously for producing different colors with a rapid manufacturing machine, it would be cumbersome to make a 3D printing machine including a different resin for every possible desired material hardness. Thus, certain embodiments employ composites that are made up of one or more individual constituent materials that can be selected or mixed together in the proper proportion before being deposited in each 3D dot of the object.

For the problem of printing (rapid prototyping) aesthetic teeth, a simpler case can be considered, since, in certain embodiments, the requirements are: a dentin support layer that is relatively elastic and opaque; a hard enamel layer with variable scattering properties; and color control through the enamel layers. In one example, this is accomplished using three different resins, along with the correct combinations of primary pigment colors.

A 3D printer capable of printing realistic, non-homogeneous objects according to an embodiment of the invention uses a combination of resins and pigments that will approximate any given set of desired material property parameters M. A transfer function T of the ideal, desired material properties is defined to yield the closest matching combination of resins and pigments that the printer has available. In general, T is likely (though not necessarily) best chosen as a non-linear function that will depend on the particular resins and pigments employed.

FIG. 1 is a flow chart 100 for a method of manufacturing an aesthetically-acceptable non-homogeneous object, according to an illustrative embodiment of the invention. In step 102, a 3D voxel representation is defined for the non-homogeneous object to be manufactured, wherein each of a plurality of voxels making up the virtual representation of the object (the virtual object) is assigned one or more values representing one or more physical properties M such as color, translucency, and hardness, for example. In step 104, the 3D voxel representation is scan converted to define a set of 3D dots, or parcels, which, when agglomerated together, will produce the shape of each of a plurality of successive Z-layers of the object to be manufactured—putting together all of the Z-layers will produce the shape of the complete object. Multivariate interpolation (e.g., trilinear interpolation) may be used in the scan conversion step 104. In addition to the shape, the 3D voxel representation also defines the one or more prescribed physical properties M at each dot making up each Z-layer of the object. These physical properties can vary throughout the object (the object is non-homogeneous), and the values of a given physical property can differ at different 3D dots. In step 106, the shape and the material properties M at each layer Z, is defined at the resolution of the 3D printer (dpi). In step 108, a transfer function T(M) is defined that identifies a resin and/or a pigment (and or combinations of the two) to produce a material having the one or more prescribed physical properties for each 3D dot to be printed. In step 110, a 3D printer deposits the pigment(s) and/or resin(s) (and/or concentrations thereof) identified by the transfer function T(M) at each dot of each of the plurality of successive Z-layers of the object, thereby producing the non-homogeneous object.

The methods described above may include depositing at least two different resins with embedded crystalline particles (e.g., of known, differing sizes or size distributions) at a given dot, the combination of which resins produces the translucency prescribed for the given dot. The deposition of dots may be repeated for a plurality of dots, e.g., all the dots making up a given Z-layer, for all the Z-layers making up the object.

Examples of voxel-based modeling systems and user interfaces (e.g., graphical and/or haptic interfaces) that can be used with the system described herein include those described in the following U.S. patents and patent applications, the texts of which are all incorporated herein by reference in their entirety: pending U.S. patent application Ser. No. 12/692,459, titled, "Haptically Enabled Coterminous Production of Prosthetics and Patient Preparations in Medical and Dental Applications," by Rawley et al., filed Jan. 22, 2010; pending U.S. patent application Ser. No. 12/321,766, titled, "Haptically Enabled Dental Modeling System," by Steingart et al., published as U.S. Patent Application Publication No. 2009/0248184; pending U.S. patent application Ser. No. 11/998,457, titled, "Systems for Haptic Design of Dental Restorations," by Steingart et al., published as U.S. Patent Application Publication No. 2008/0261165; pending U.S. patent application Ser. No. 11/998,877, titled, "Systems for Hybrid Geometric/Volumetric Representation of 3D Objects," by Faken et al., published as U.S. Patent Application Publication No. 2008/0246761; U.S. Pat. No. 7,149,596, titled, "Apparatus and Methods for Modifying a Model of an Object to Enforce Compliance with a Manufacturing Constraint," by Berger et al.; U.S. Pat. No. 6,958,752, titled, "Systems and Methods for Three-Dimensional Modeling," by Jennings, Jr. et al.; U.S. Pat. No. 6,867,770, titled, "Systems and Methods for Voxel Warping," by Payne; U.S. Pat. No. 6,421,048, titled, "Systems and Methods for Interacting With Virtual Objects in A Haptic Virtual Reality Environment," by Shih et al.; and U.S. Pat. No. 6,111,577, titled, "Method and Apparatus for Determining Forces to be Applied to a User Through a Haptic Interface," by Zilles et al.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A system for fabricating a non-homogeneous article, the system comprising:
a design application configured to create a 3D voxel-based model of the non-homogeneous article, wherein
the 3D voxel-based model comprises a multi-dimensional array of voxel elements, wherein
each voxel element of the multi-dimensional array of voxel elements is assigned one or more values representing one or more physical properties M; and
a rapid prototyping machine for fabrication of the non-homogeneous article, wherein said rapid prototyping machine is configured to fabricate the non-homogeneous article via additive manufacturing using the 3D voxel-based model, wherein
the rapid prototyping machine is configured to fabricate the non-homogenous article using one or more materials; and the one or more physical properties of the voxel elements of the multi-dimensional array of voxel elements correspond to properties of a plurality of 3D dots of the non-homogeneous article, wherein for each 3D dot of the plurality of 3D dots, a respective transfer function T(M) identifies at least one of the one or more materials to produce a material having the respective one or more physical properties of the respective 3D dot;

wherein fabricating the non-homogenous article comprises curing a resin identified by the transfer function associated with at least a portion of the dots of the plurality of 3D dots, wherein the transfer function associated with the portion of the dots identifies at least one light frequency for curing the respective dot.

2. The system of claim 1, wherein the physical properties comprise at least one of color, translucency, hardness, modulus, and dynamic modulus.

3. The system of claim 1, wherein the system is configured to perform additive manufacturing by providing successive layers or parcels of material.

4. The system of claim 1, further comprising a user interface in communication with the design application, wherein the user interface is configured to receive input from a user.

5. A system for fabricating a non-homogenous article, the system comprising:

a 3D printer configured to fabricate the non-homogenous article;

a processor; and a memory having instructions stored thereon, wherein the instructions, when executed, cause the processor to:

receive a 3D voxel-based model of the non-homogenous article, wherein the 3D voxel-based model comprises a multi-dimensional array of voxel elements, wherein each voxel element of the multi-dimensional array of voxel elements is assigned one or more values representing one or more physical properties;

based upon the 3D voxel-based model, define a plurality of 3D dots, wherein each dot of the plurality of 3D dots comprises a respective one or more physical properties, wherein the respective one or more physical properties are defined at a resolution of the 3D printer, and the plurality of 3D dots, upon agglomeration as one or more materials deposited by the 3D printer, are configured to produce the shape of the non-homogenous article;

determine, for each 3D dot of the plurality of 3D dots, a respective transfer function T(M), wherein the respective transfer function identifies the one or more materials, and the one or more materials, when deposited by the 3D printer, are configured to produce a closest matching material to a material having the one or more prescribed physical properties associated with the respective 3D dot; and provide instructions to the 3D printer, based upon the plurality of 3D dots, to produce the non-homogenous article;

wherein the 3D printer is configured to deposit each dot of the plurality of 3D dots as the one or more materials, and producing the non-homogenous article comprises curing a resin identified by the transfer function associated with at least a portion of the dots of the plurality of 3D dots, wherein the transfer function associated with the portion of the dots identifies at least one light frequency for curing the respective dot.

6. The system of claim 5, wherein the one or more materials comprise at least one of a pigment and an ink.

7. The system of claim 5, wherein the 3D printer comprises at least one of the processor and the memory.

8. The system of claim 5, wherein the transfer function T(M) identifies at least one of multiple pigments, multiple inks, and multiple resins.

9. The system of claim 5, wherein the transfer function T(M) identifies a combination of primary ink colors.

10. The system of claim 5, wherein the transfer function T(M) identifies a mixing proportion for combining at least two of the one or more materials.

11. The system of claim 5, wherein closeness of matching of the material is dependent upon one or more of a) capabilities of the 3D printer, b) one or more resins available to the 3D printer, c) one or more pigments available to the 3D printer, and d) one or more inks available to the 3D printer.

12. The system of claim 5, wherein defining the plurality of 3D dots comprises using multivariate interpolation to define the one or more physical properties at each respective 3D dot.

13. The system of claim 12, wherein the multivariate interpolation is trilinear interpolation.

14. The system of claim 5, wherein the 3D printer is a rapid prototyping device.

15. The system of claim 5, further comprising:

a user interface; and a design application, wherein the design application is configured to define the 3D voxel-based model based in part upon input received from a user via the user interface.

16. The system of claim 15, wherein the memory comprises the design application.

* * * * *